United States Patent [19]

Henning et al.

[11] Patent Number: 5,399,686

[45] Date of Patent: Mar. 21, 1995

[54] LORACARBEF ISOPROPANOLATE AND A PROCESS FOR CONVERTING LORACARBEF ISOPROPANOLATE TO LORACARBEF MONOHYDRATE

[75] Inventors: William C. Henning; Michael E. O'Dea, both of Lafayette, Ind.

[73] Assignee: Eli Lilly and Company, Indianapolis, Ind.

[21] Appl. No.: 72,204

[22] Filed: Jun. 4, 1993

[51] Int. Cl.$^6$ .................. C07D 487/04; A61K 31/435
[52] U.S. Cl. ............................................. 540/205
[58] Field of Search ............................... 540/205

[56] References Cited

U.S. PATENT DOCUMENTS

| | | | |
|---|---|---|---|
| 3,502,663 | 3/1970 | Barnes | 260/243 |
| 3,531,481 | 9/1970 | Pfeiffer | 540/205 |
| 4,977,257 | 12/1990 | Eckrich et al. | 260/243 |

FOREIGN PATENT DOCUMENTS 0311366 5/1988 European Pat. Off. .
0369686 10/1989 European Pat. Off. .

Primary Examiner—Nicholas Rizzo
Attorney, Agent, or Firm—Thomas G. Plant; James J. Sales; Gerald V. Dahling

[57] ABSTRACT

The invention is directed to the crystalline isopropyl alcohol solvate of loracarbef, and also is directed to a process for the preparation of the crystalline monohydrate form of the compound of formula (I)

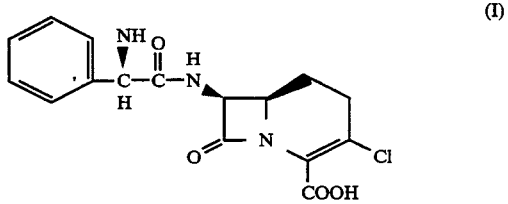

which includes exposing the crystalline isopropyl solvate form of the compound of formula (I) to a temperature of between about 50° and 90° C. and a relative humidity of between about 60 to about 100%.

3 Claims, No Drawings

LORACARBEF ISOPROPANOLATE AND A PROCESS FOR CONVERTING LORACARBEF ISOPROPANOLATE TO LORACARBEF MONOHYDRATE

BACKGROUND OF THE INVENTION

This invention relates to a process for the preparation of crystalline loracarbef monohydrate.

The β-lactam antibiotic of the formula (I)

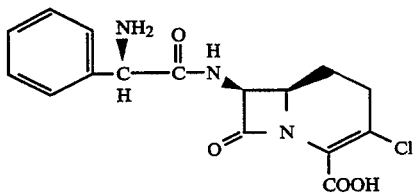

(I)

is the potent orally active antibiotic known as loracarbef. The antibiotic is described, for example, by Hashimoto et al. in U.S. Pat. No. 4,335,211, issued Jun. 15, 1982.

The above compound comes in various forms, including the crystalline monohydrate form, which is disclosed in European Patent Publication 0,311,366 having a publication date of Apr. 12, 1989. Other known solvate forms of the compound are disclosed in Eckrich et al. U.S. Pat. No. 4,977,257. The crystalline dihydrate form of loracarbef is disclosed in European Patent Publication 0,369,686 having a publication date of May 23, 1990. As indicated in the EPO application, the crystalline monohydrate may be prepared by first suspending the dihydrate in water and effecting solution by the addition of acid followed by the adjustment of the pH with base, or by the addition of base followed by acid.

It has been determined that loracarbef crystalline monohydrate is a fine "hair-like" crystal which results in very slow filtration. In filtering the monohydrate, the crystals tend to from a mat on the filter medium which prevents or reduces the ability to complete filtration, such that the crystals must be washed with water. As loracarbef monohydrate is moderately soluble in water, (approximately 10 mg/ml), loss of yield results when such washes are needed.

What is needed in light of the above difficulties is a process for preparing crystalline loracarbef monohydrate in a more efficient manner, that is, to avoid the requirement of filtering the crystalline monohydrate.

SUMMARY OF THE INVENTION

The invention is directed to the crystalline isopropyl alcohol solvate of loracarbef. The invention also provides a process for the preparation of the crystalline monohydrate form of the compound of formula (I)

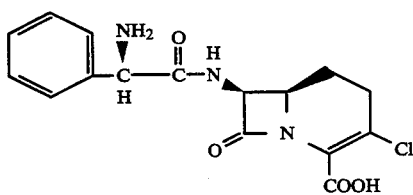

(I)

which comprises exposing the crystalline isopropanolate form of a compound of formula (I) to a temperature between about 50° to about 90° C. and a relative humidity of between about 60 to about 100%.

DESCRIPTION OF THE INVENTION

The instant invention is directed to the crystalline isopropyl alcohol solvate of the compound of Formula I:

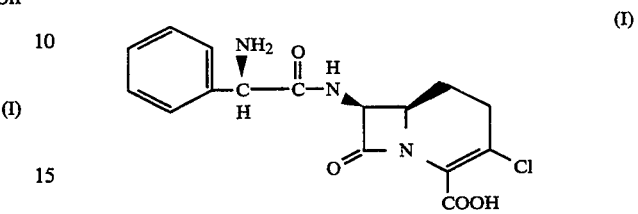

(I)

In the present solvate of formula (I), the C-2' asymmetric center has the R absolute configuration. Furthermore, the instant solvate may encompass the zwitterionic form of the compound of formula (I).

A preferred embodiment of the invention is a crystalline isopropyl alcohol solvate of loracarbef exhibiting the X-ray powder diffraction pattern below:

| Isopropanolate | |
| --- | --- |
| d | I/I$_1$ |
| 12.4026 | 55.36 |
| 7.5680 | 100.00 |
| 6.7278 | 1.29 |
| 6.5450 | 1.71 |
| 6.0063 | 1.58 |
| 5.5590 | 1.37 |
| 5.3539 | 2.24 |
| 5.2350 | 1.67 |
| 4.9480 | 2.35 |
| 4.7082 | 2.67 |
| 4.5995 | 2.55 |
| 4.3208 | 3.50 |
| 4.2571 | 11.18 |
| 3.9657 | 8.14 |
| 3.9313 | 16.69 |
| 3.9056 | 14.04 |
| 3.8634 | 1.57 |
| 3.7704 | 7.64 |
| 3.6572 | 4.46 |
| 3.6319 | 4.69 |
| 3.5208 | 5.28 |
| 3.4257 | 1.66 |
| 3.3394 | 0.84 |
| 3.2530 | 1.07 |
| 3.2195 | 2.45 |
| 3.1787 | 4.00 |
| 3.0818 | 1.01 |
| 3.0203 | 2.70 |
| 2.9972 | 1.02 |
| 2.8850 | 7.52 |
| 2.7979 | 0.98 |
| 2.7699 | 3.28 |
| 2.7294 | 0.81 |
| 2.6378 | 3.18 |
| 2.5751 | 2.26 |

The diffraction pattern above was obtained with a copper radiation source in a Peltier cooled Si(Li) solid state detector. The tube voltage was set at 50 kV, the tube current was set at 40 mA, the aperture diaphragm was set at a 0.06 mm slit, the scattered radiation diaphragm was set at a 1 mm slit, the detector diaphragm had a 0.1 mm slit, the scanning rate for the step scan instrument was 0.04 degree/step two theta for 2.5 sec/step, and the scanning range was 4.0 to 35.0 degrees two theta. The background was electronically subtracted, the peak width was set at 0.3 and threshold at 3.0 for peak search.

It was discovered that using a high relative humidity in combination with high temperatures produced a solid state conversion from the isopropanolate to monohydrate. This discovery provided a process to avoid isolation of the monohydrate through filtration, as the monohydrate may be isolated through forming the isopropanolate which then may undergo the solid state conversion to the monohydrate. Also, there is no need to crystallize the monohydrate from solution using acid or base, as previously described.

The isopropanolate may be prepared through general means known in the art. The isopropanolate may be readily prepared by suspending any form of loracarbef in isopropanol or aqueous isopropanol and forming a solution. A solution is usually effected by the addition of an acid, although a solution may also be caused by the addition of a base. The desired isopropanolate may then be precipitated by the adjustment of the pH to approximately 5.8 to 6.2 by using an acid (such as hydrochloric, hydrobromic or sulfuric) or base (such as triethylamine), at a temperature of 20° C. to 25° C. The isopropanolate is collected, typically by filtration, and dried to provide the isopropanolate.

The solid state conversion from the isopropanolate to monohydrate takes place in an environment of both elevated temperature, from about 50° to about 90° C., and at high relative humidities, from about 60 to about 100%. A preferred temperature range is between about 55° to about 65° C. A preferred humidity range is between about 80 and 100%.

Microscopically, the crystals can be seen changing from isopropanolate to the monohydrate during the conversion. The X-ray diffraction patterns of the resulting materials had patterns that compared favorably to that of the monohydrate reference pattern.

EXPERIMENTAL SECTION

Example 1

Loracarbef Isopropanolate

Isopropyl alcohol (660.0 ml), deionized water (67.0 ml), loracarbef bis(DMF)solvate (50.0 g) and hydrochloric acid (15.6 g) are combined and stirred at a temperature of 20°-25° C., (If needed, more hydrochloric acid may be added to complete dissolution). Deionized water (10.0 ml) and activated carbon (2.0 g) are added to the mixture.

The flask is stirred for one hour. To the mixture is added, over at least 2 hours, ammonia (28%, 12.6 g) to precipitate the isopropanolate, and the mixture is filtered. The filter cake is washed with 127.0 ml of isopropanol, followed by a water wash (85.0 ml) and the wet cake is dried in a vacuum oven at 40°-45° C. to result in the titled product.

Example 2

Loracarbef Monohydrate

A Kugelrohr distillation apparatus is set up, consisting of a Kugelrohr oven with a time proportioning temperature controller, Type J thermocouple, 300 mm Allihn condenser attached to a constant temperature bath, a Kugelrohr distillation agitation motor and a Büchi pressure controller.

A sample of loracarbef isopropanolate is charged to the 300 mm. Allihn condenser. Deionized water (200 g) is charged to a 1 L., 1-neck, round bottom flask. The flask is placed in the Kugelrohr oven and connected to the condenser. The system's pressure is pulled down to approximately 300 mbar. The jacket on the condenser is heated to 75° C. with a constant temperature bath. The Kugelrohr oven is heated to 65° C. The system's pressure is further reduced to 250 mbar and the isopropanolate is subjected to a relative humidity of 100% with agitation for approximately 6 to 8 hours. The oven and condenser are cooled to 20°-25° C. The system is vented to atmospheric pressure. The hydrated product is removed and placed in a vacuum oven at 40°-45° C. The product is dried overnight under full vacuum with a slight nitrogen sweep.

Example 3

Loracarbef Isopropanolate

Loracarbef bis(DMF)solvate (70.50 g., 50.05 base g.), isopropanol (520.0 g) and deionized water (88.8 g) (the original charge plus the carbon slurry amount of water) are charged to a 2 L jacketed 3-neck round bottom flask. Hydrochloric acid is then charged to the slurry to completely dissolve the solvate. Dissolution is complete at a pH of 0.90.

To the solution is charged activated carbon powder (2.0 g). The flask contents are stirred for one hour at 20°-25° C. and then filtered over a 9 cm Büchner funnel pre-coated with a filter aid, such as Hyflo. The filtrate is returned to the jacketed flask and ammonia (28%, 12.7 g), is added dropwise over 4 hours via a syringe pump. Crystal size is large which is consistent with previous isopropanolate material.

The slurry is stirred for one hour at 20°-25° C. and filtered over Whatman #1 filter paper (Filtration time: 2:04 min). The wet cake is washed with isopropanol and water. The washed material is dried overnight in a vacuum oven at 40°-45° C. under full vacuum and a nitrogen sweep.

Example 4

Loracarbef Isopropanolate

Isopropanol (440 L), deionized water (25 L), hydrochloric acid (10 kg), and loracarbef bis(DMF) solvate (42.3 kg) are combined in a tank. The tank walls are then rinsed with 22 L of deionized water. The mixture is stirred for 15 minutes and hydrochloric acid in 500 g increments is added to complete solution. A total of 2 kilograms of hydrochloric acid is added until disolution is completed, and the mixture has a pH of 0.7.

Activated carbon (1.5 kg) slurried in 6 L of $H_2O$ is added to the tank and the mixture is stirred for 20 minutes and then filtered. The tank is rinsed with 10 liters of deionized water. Ammonia (28%), is added Until the pH is raised to between 5.8 to 6.2. The crystallized isopropanolate is filtered and washed with isopropyl alcohol. The filter cake is dried in a vacuum dryer at a temperature of between 42° and 48° C.

Example 5

Loracarbef Monohydrate

The conversion of the material in Example 4 to loracarbef monohydrate is carried out by setting the drier temperature to between 65° and 75° C., setting the vacuum control on the drier to 4 psia, and injecting steam into the drier to maintain humidity in a range of 95 to 100%. After one hour at these conditions some of the content of the drier is cooled and a sample is taken. The conditions for conversion to loracarbef monohydrate, above, are set in place for 3 hours at which time indications are that conversion of the loracarbef monohydrate is complete. The material is then dried at full vacuum (0.7 psia) and at 45° C. for approximately 8 hours.

We claim:

1. A process for the preparation of the crystalline monohydrate form of the compound of formula (I)

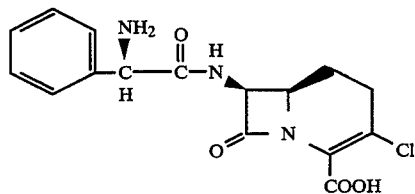

which comprises exposing the crystalline isopropanolate form of the compound of formula (I) to a temperature of between about 50° to about 90° C. and a relative humidity of between about 60 to about 100%.

2. The process as recited in claim 1 wherein said relative humidity is between about 80 to about 100%.

3. The process as recited in claim 2 wherein said temperature is between about 55° to about 65° C.

* * * * *